US00PP37459P2

(12) United States Plant Patent
Hansen

(10) Patent No.: US PP37,459 P2
(45) Date of Patent: Jun. 9, 2026

(54) ***PENSTEMON* PLANT NAMED 'Dark Amethyst'**

(50) Latin Name: *Penstemon schmidel*
Varietal Denomination: Dark Amethyst

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/831,920

(22) Filed: Nov. 13, 2025

(51) Int. Cl.
*A01H 6/68* (2018.01)
*A01H 5/02* (2018.01)

(52) U.S. Cl.
USPC ..... Plt./465

(58) Field of Classification Search
USPC ..... Plt./465
CPC ..... A01H 6/68; A01H 5/02
See application file for complete search history.

*Primary Examiner* — Keith O. Robinson

(57) ABSTRACT

The new and distinct cultivar of *Penstemon* plant named 'Dark Amethyst' with rounded mound with upright heavily-branched peduncles producing dark reddish-purple petals with light purple throats beginning in early summer for about four weeks and repeating in late summer if dead-headed. The lanceolate foliage is bluish-green, and the plant is winter hardy to at least USDA zone 6. The new plant is useful in the landscape as a specimen plant, en masse or container plant, and attractive to hummingbirds.

2 Drawing Sheets

Botanical classification: *Penstemon schmidel.*
Variety denomination: 'Dark Amethyst'.

STATEMENT REGARDING PRIOR DISCLOSURES UNDER 37 CFR 1.77(B)(6)

The first offer for sale was made by Walters Gardens, Inc. to Prides Corner Farm on Nov. 25, 2024. Walters Gardens, Inc. obtained the new plant and all information relating thereto, from the inventor. No plants of *Penstemon* 'Dark Amethyst' have been sold anywhere in the world by any name nor has any disclosure of the new plant been made more than one year prior to the filing date of this application, and such sale or disclosure within one year was either derived directly or indirectly from the inventor.

BACKGROUND OF THE INVENTION

The present invention relates to a new and distinct plant of Beardtongue, botanically known as *Penstemon* 'Dark Amethyst' and will be referred to hereinafter also by its cultivar name 'Dark Amethyst' and as the new plant. The new plant cultivar of Beardtongue is a hardy herbaceous perennial grown for landscape use.

*Penstemon* 'Dark Amethyst' is a single seedling selection derived from a cross between 'Red Riding Hood' U.S. Plant Pat. No. 18,950 as the female parent and 'Purple Riding Hood' U.S. Plant Pat. No. 23,067 as the male parent on Jun. 21, 2013, at a wholesale perennial nursery in Zeeland, Michigan. Seed was collected in late summer of 2013. All subsequent evaluations were performed in a full-sun trial garden at the same nursery with loamy-sand soil and irrigation and fertilizer as required. The individual seedling was assigned the breeder code 13-15-3 while being selected for further trials during the summer of 2015. The new plant was propagated by basal shoot cuttings at the same nursery in Zeeland, MI, and the original plant and the cuttings were evaluated over the next six years until final approval for introduction in the summer of 2021. The resultant asexually propagated cuttings have been stable and identical to the original plant in successive generations.

SUMMARY OF THE INVENTION

*Penstemon* 'Dark Amethyst' differs from its parents as well as all other hardy Beardtongue known to the inventor in a combination of traits. The following characteristics in combination distinguish 'Dark Amethyst' from all other beardtongue plants known to the inventor:

1. Round mounded growth with tightly-compact strong upright stems;
2. Glaucous lanceolate foliage developing and maintaining a deep bluish-green coloration in high light intensity;
3. Dense panicles producing numerous flowers with dark reddish-purple petals and a light purple throat;
4. Flowers for four weeks beginning early summer in Michigan and repeating in late summer if deadheaded;
5. Winter hardy to at least USDA zone 6.

The nearest comparison cultivars are: 'Balrocurp' U.S. Plant Pat. No. 35,761, 'Cha Cha Purple' (not patented), 'Crushed Grapes' U.S. Plant Pat. No. 18,233, 'P008S' (aka. RED ROCKS®) (not patented), 'Grape Taffy' U.S. Plant Pat. No. 22,567, 'P007S' (not patented), and 'Sweet Grapes' U.S. Plant Pat. No. 13,549.

'Balrocurp' has a shorter habit and the flowers are more reddish-purple with a whiter inner corolla tube. 'Cha Cha Purple' has taller habit flowers that are lighter purple on less dense and less rigid panicles, 'Crushed Grapes' has a much shorter habit and the peduncle is shorter with fewer flowers of more reddish-purple. 'P008S' has a slightly taller habit, the flowers are slightly lighter rosy-red, broader with flatter labia lobes, and the inner corolla tube is nearly white. 'Grape Taffy' has a shorter habit with shorter peduncles producing fewer flowers of more reddish-purple and is less winter hardy. 'P007S' has a taller habit, the flowers are lighter purple and have a white throat. 'Sweet Grapes' is shorter in habit and the flowers are more reddish-purple.

The female has a taller habit and more reddish-colored flowers. The male or pollen parent has a shorter habit and the peduncle produces fewer flowers of more bluish.

Plants of 'Balrocurp', 'Crushed Grapes', 'Sweet Grapes', 'Red Riding Hood', and 'Purple Riding Hood' are less persistent in the landscape.

BRIEF DESCRIPTION OF THE DRAWINGS

The photographs of the new plant demonstrate the overall appearance of the new plant, including the unique traits. The colors are as accurate as reasonably possible with color reproductions. Ambient light spectrum, source, temperature, and direction may cause the appearance of minor variations in color. The plants used in the photograph are two-year-old plants grown in full-sun loamy-sand soil in trial gardens of a nursery in Zeeland, Michigan.

DETAILED BOTANICAL DESCRIPTION

Figure 1:
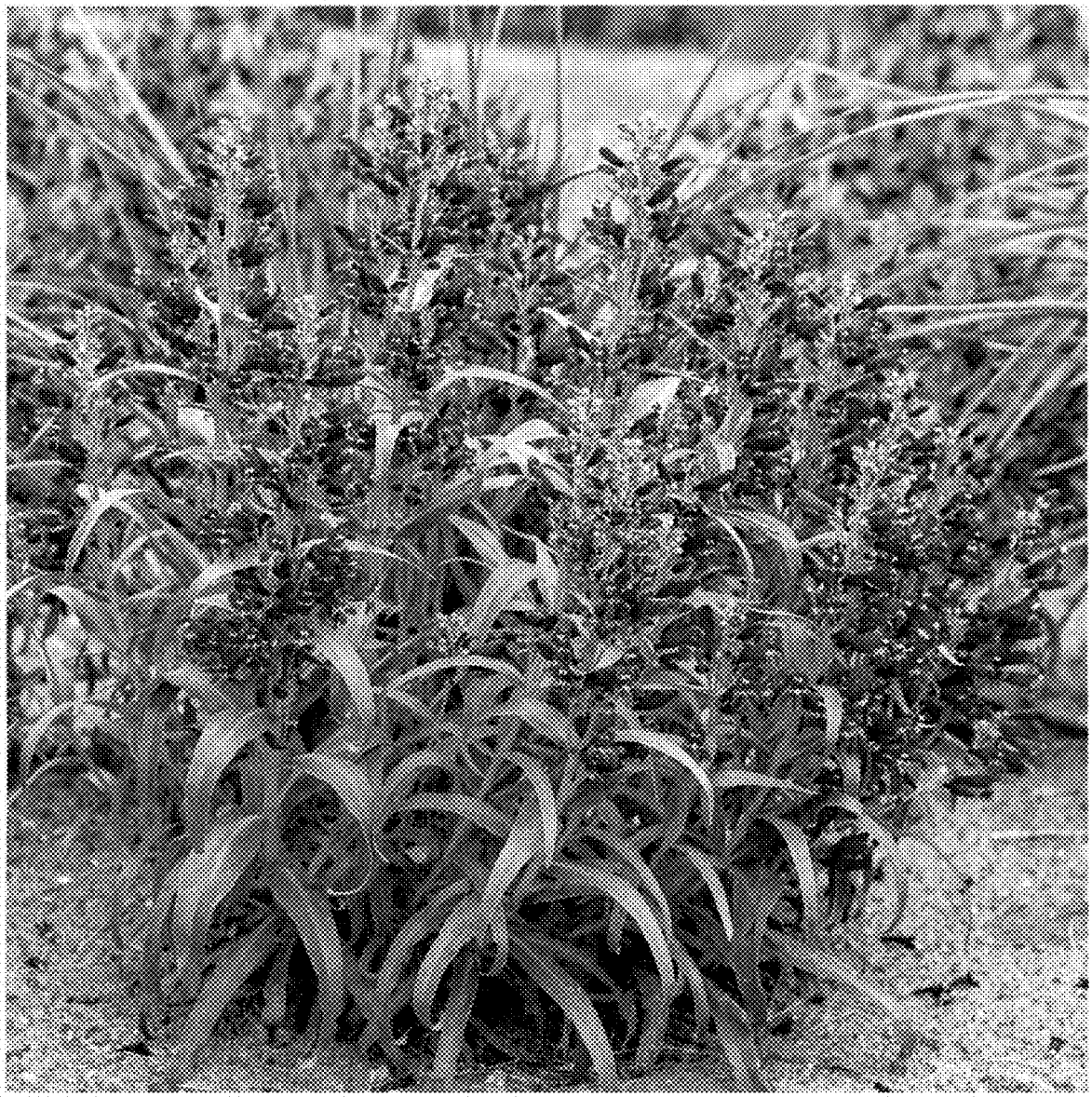
FIG. 1 shows the new plant in a trial garden landscape in early flower production.
Figure 2:
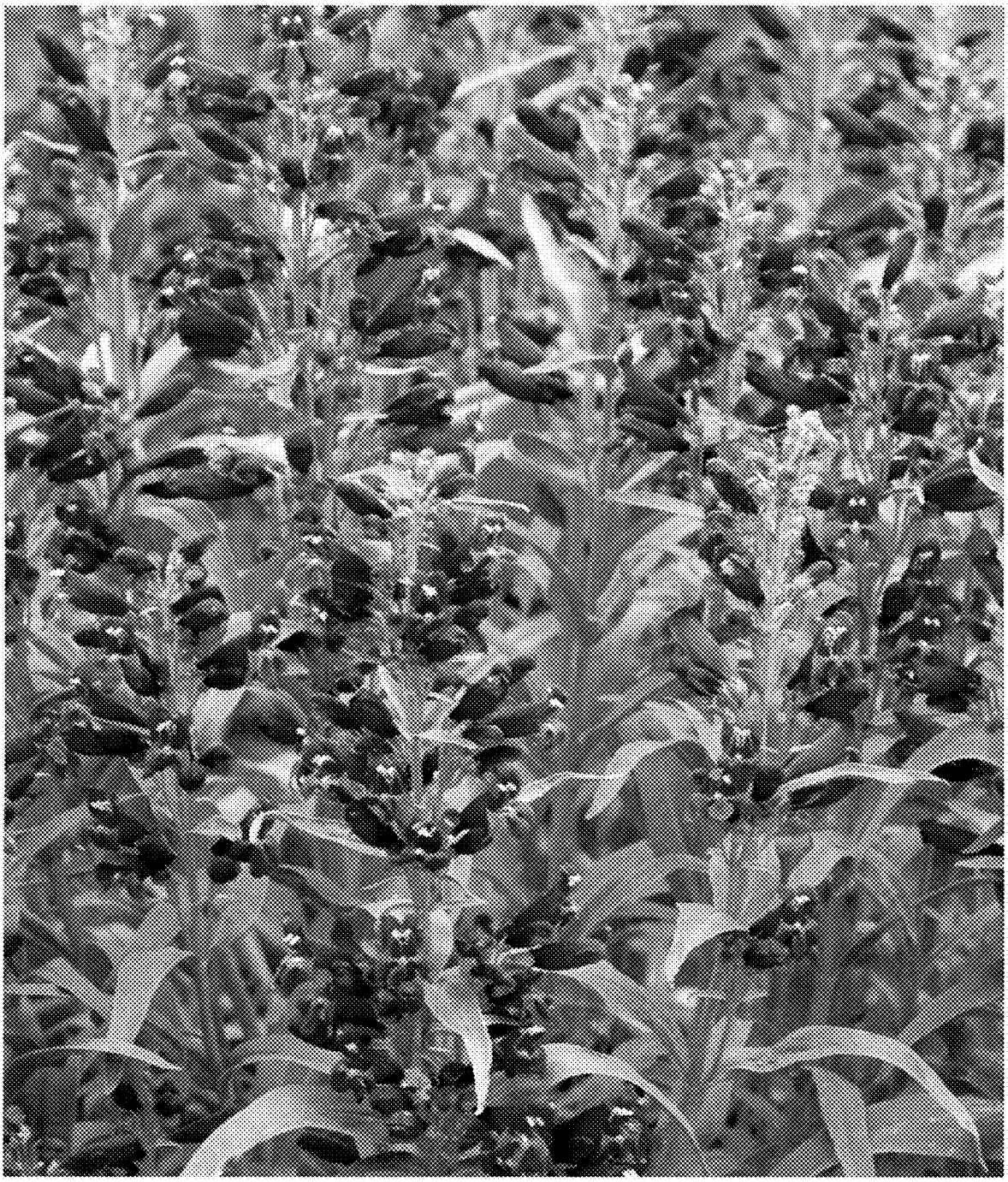
FIG. 2 shows a close-up of the flowers and buds.

The following is a detailed description of *Penstemon* 'Dark Amethyst' as observed and compared to other cultivars for two years in trial gardens and production fields at a nursery in Zeeland, Michigan. The following description is of a two-year-old plant growing in a full-sun display garden in Zeeland, MI with limited supplemental fertilizer and irrigation as needed and without any pinching or plant growth regulators. The new plant has not been observed under all possible environments, and the phenotype may vary slightly with different environmental conditions, such as temperature, light, fertility, moisture, and maturity levels, but without any change in the genotype. The color descriptions are in accordance with the 2015 edition of The R.H.S. Colour Chart of The Royal Horticultural Society, London, England, except where common dictionary color terms are used.

Parentage: The female (seed) parent is 'Red Riding Hood' and the male (pollen) parent is 'Purple Riding Hood';

Plant habit: Herbaceous winter-hardy, perennial with upright rigid stems emerging from the mounded base in the spring; up to about 12 stems per plant; flowering in branched panicle;

Plant size: To about 47 cm in height, average stem 44 cm tall, and about 51 cm in width about at the soil;

Root description: Fibrous, well-branched, developing to about 1 mm thick; color between RHS 161A and RHS 161B;

Propagation: Shoot-tip cuttings; root initiation occurs in about 14 days at a temperature of 22° C.;

Growth rate: Moderately vigorous;

Crop time: About 12 to 14 weeks to finish in a 3.8-liter pot from a rooted plug;

Stem description: Cylindrical; oppositely branched in the distal region; glabrous; glaucous; to about 47 cm long and about 7 mm diameter at base;

Stem color: Between RHS 138A and RHS N138B;

Node: About 4 per stem below flowers, average internode length about 2.5 cm, larger distally; diameter about 8 mm;

Node color: Between RHS 138A and RHS N138B;

Foliage description: Simple; lanceolate; glabrous; slightly glaucous and lustrous adaxial, and slightly glaucous abaxial; sessile with attenuate base; margin entire; fragrance not detected;

Leaf size: Leaves to about 145 mm long and about 24 mm wide;

Leaf color: Young expanding adaxial and abaxial between RHS N138A and RHS 132A; mature adaxial nearest RHS 137A, abaxial between RHS N138C and RHS N148B;

Leaf venation: pinnate;

Vein color: Young abaxial midrib and primary veins nearest RHS 146D, young abaxial midrib between RHS 145C and RHS 147D and secondary veins nearest RHS 147D; mature adaxial midrib nearest RHS 147C and secondary veins nearest RHS 137A; mature abaxial proximal two-thirds between RHS 145D and RHS 147D, distal midrib and secondary veins nearest RHS 146D;

Petiole: Sessile;

Inflorescence: Panicle; flowering portion to about 25 cm long and about 7.5 cm across;

Pedicel: Cylindrical; glabrous, lustrous; between 5 and 13 mm long, and 1 mm diameter;

Pedicel color: Nearest RHS 146C;

Peduncle: Branched panicle with up to 24 branches; smooth, glabrous; main stems vertical; to about 43 cm tall and 8 mm diameter base flowering in upper 25 cm; to about 275 flowers per stem and 32 flowers per branch;

Branches: Cylindrical; glabrous; to 15 cm long and 2.5 mm diameter at base;

Peduncle and branch color: Between RHS 146D and RHS 148C;

Flower buds about one day prior to opening: About 25 mm long, about 6 mm diameter distally, and 3 mm diameter near the base; clavate; rounded apex; basal 3 mm of corolla tube narrowed to about 3 mm diameter, with rounded base;

Bud color: Proximal 3 to 4 mm of corolla tube between RHS 145C and RHS 145D, and distal 3 mm between RHS 86A and RHS N89A, ventral central portion between RHS N81C and RHS N81B, dorsal central portion between RHS 83A and RHS N81A;

Flowering season: Beginning in early summer for about four weeks, repeating if deadheaded;

Flowers: Zygomorphic; perfect; complete; bilabiate with upper and lower lip gamopetalous in about basal 20 mm; about 30 mm long and about 13 mm across and 15 mm tall at the face; face flat when first open, dorsal lobes becoming slightly reflexed and longitudinally folded in ventral lobes; lasting about five to seven days; self-cleaning;

Flower attitude: Mostly outwardly;

Flower fragrance: None detected;

Corolla: Bilabiate; ventral petal with three lobes; dorsal petal with two lobes; glabrous abaxial; glabrous adaxial dorsal petal and fused tube portion except pubescent on an adaxial ventral petal in the distal portion near mouth; dorsal labium lobes about 4 mm long and 4 mm across at fusion with rounded apices; two lateral lobes on ventral labium about 7 mm long and 5 mm wide at division just beyond midpoint between fusion and apex, center ventral lobe about 7 mm long and 4.5 mm across; all lobes with rounded apices and entire margins; corolla tube about 20 mm long, 8 mm wide and 8 mm tall at fusion and 4 mm diameter at base;

Corolla color: Dorsal and ventral labium mature adaxial proximal 2 mm of corolla tube nearest RHS 145D, next 5 mm transitioning from nearest RHS 84D to nearest RHS N81B, center 4 mm nearest RHS 84D with ventral labium veined nearest RHS 83B, ventral lobes nearest RHS 83B and dorsal lobes nearest RHS; dorsal and ventral abaxial proximal 2 mm nearest RHS 145D, next 5 mm between RHS 72A and RHS 72B, distally nearest RHS 83D when mature and when young and nearest RHS 72A with regions transitioning to between RHS 72A and RHS 83D with three ventral lobes nearest RHS 83D; young ventral labium adaxial corolla proximal 2 mm nearest RHS 145D, next 4 mm nearest RHS 72B, middle 12 mm nearest RHS 84D with veins nearest RHS N81A and lobes nearest RHS N81A; young distal labium adaxial corolla proximal 2 mm nearest RHS 145D, next 4 mm nearest RHS 72B, middle 12 mm nearest RHS 84D, and lobes between RHS 86A and RHS N88A;

Gynoecium: Single; superior; persistent after corolla drops; about 20 mm long;

*Style*.—Cylindrical; glabrous; arcuate slightly downwardly distally; about 16 mm long and about 0.5 mm diameter; color proximally nearest RHS NN155B developing distally with maturity to between RHS 77A and RHS N79C.

*Stigma*.—Semi-globose, to about 0.5 mm diameter; color nearest RHS N155B.

*Ovary*.—Oblong conical; with truncate base and acute apex; lustrous; about 4 mm long and 2 mm across at base; color between RHS N144D and RHS 145A.

Androecium: Four; didynamous; slightly arcuate;

*Filaments*.—Cylindrical; glabrous; lustrous; longer set about 24 mm long and 1 mm diameter, adnate inner corolla in basal 8 mm; shorter set about 22 mm long and 1 mm diameter, adnate inner corolla in basal 1 mm; color nearest RHS NN155C except proximal 2 mm nearest RHS 145C.

*Anther*.—Elliptic; basifixed; longitudinal; micro-puberulent on exterior surface; bent at filament attachment; about 4 mm long and 1 mm across; color nearest RHS 11D.

*Staminode*.—Single; cylindrical; about 21 mm long and 0.5 mm diameter; adnate to inner corolla tube in basal 6 mm; glabrous except tufted in distal 2 mm; color nearest RHS NN155B.

*Pollen*.—Abundant; color nearest RHS NN155B.

Calyx: Campanulate; adpressed to corolla; about 5 mm long and about 4 mm across at apex;

Sepals: Five; ovate; glabrous adaxial and abaxial; acute apex and fused in basal 1.5 mm; entire margin; to about 2.5 mm wide above fusion point and 5 mm long;

Sepal color: Adaxial and abaxial nearest RHS 137B with margins nearest RHS;

Fruit: Septicidal capsule; ovoid with acute apex and rounded base; to about 10 mm long and 5 mm across; color variable at maturity nearest RHS 199C and nearest RHS N200A;

Seed: Irregular; flattened; glabrous dried; about 2 mm long, 1.5 mm wide, and about 0.3 mm thick; color nearest RHS 200A;

Hardiness to at least U.S.D.A. zones 4 to 8; the new plant performs best with good drainage and is resistant to drought once established;

Pest and disease resistance: Resistance beyond that typical of beardtongue plants has not been observed. No other susceptibility or resistance to diseases or pests has been observed except that which is common to *Penstemon*.

It is claimed:

1. A new and distinct cultivar of *Penstemon* plant named 'Dark Amethyst' as herein described and illustrated.

* * * * *